(12) United States Patent
Kato et al.

(10) Patent No.: US 7,150,986 B2
(45) Date of Patent: Dec. 19, 2006

(54) LACTIC ACID BACTERIA-CONTAINING PROBIOTICS PRODUCTS

(75) Inventors: Azusa Kato, Tokyo (JP); Seigo Nakaya, Tokyo (JP); Nobuyuki Suzuki, Tokyo (JP); Haruhisa Hirata, Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 453 days.

(21) Appl. No.: 10/372,323

(22) Filed: Feb. 25, 2003

(65) Prior Publication Data

US 2003/0157079 A1 Aug. 21, 2003

Related U.S. Application Data

(63) Continuation of application No. PCT/JP01/07312, filed on Aug. 27, 2001.

(30) Foreign Application Priority Data

Aug. 25, 2000 (JP) .............................. 2000-254775

(51) Int. Cl.
*A61K 45/00* (2006.01)
(52) U.S. Cl. ................................. 435/252.9; 424/93.45
(58) Field of Classification Search ..................... None
See application file for complete search history.

(56) References Cited

U.S. PATENT DOCUMENTS 4,746,512 A 5/1988 Kawai et al.

FOREIGN PATENT DOCUMENTS

| EP | 0 861 905 | 9/1998 |
|---|---|---|
| EP | 0 956 858 | 11/1999 |
| JP | 9-241173 | 9/1997 |
| JP | 2001-158743 | 6/2001 |
| WO | WO 00/35465 | 6/2000 |

OTHER PUBLICATIONS

Colum Dunne, et al., "Probiotics: from myth to reality. Demonstration of functionality in animal models of disease and in human clinical trials", Antonie van Leeuwenhoek, vol. 76, No. 1-4, XP-001015705, 1999, pp. 279-272.

Pirkka V. Kirjavainen, et al., "The ability of probiotic bacteria to bind to human intestinal mucus", FEMS Microbiology Letters, vol. 167, No. 2, XP-002247857, Oct. 15, 1998, pp. 185-189.

Mary Ellen Sanders, et al., "Bringing a Probiotic-Containing Functional Food to the Market: Microbiological, Product, Regulatory and Labeling Issues," *Antonic Van Leeuwenhoek*, 1999, vol. 76, pp. 293-318.

Virginia S. Ocana, et al., "Characterization of a Bacteriocin-Like Substance Produced by a Vaginal Lactobacillus Salivarius Strain," *Applied and Environmental Microbiology*, vol. 65, No. 12, Dec. 1999, pp. 5631-5635.

*Primary Examiner*—Irene Marx
(74) *Attorney, Agent, or Firm*—Oblon, Spivak, McClelland, Maier & Neustadt, P.C.

(57) ABSTRACT

The present invention provides a probiotics product comprising, as an effective component, lactic acid bacteria belonging to *Lactobacillus salivarius* possessing high adhesiveness to mucous membrane, a high proliferation ability and a high resistance to acids, a composition for preventing and/or treating digestive tract's diseases comprising the probiotics product as an effective component and a novel *Lactobacillus salivarius* strain possessing high adhesiveness to mucous membrane, a high proliferation ability and a high resistance to acids. The lactic acid bacteria and the probiotics product and the composition for preventing and/or treating digestive tract's diseases, which contain the lactic acid bacteria as an effective component, according to the present invention can sufficiently show their probiotics functions without being easily discharged from the digestive tract and urinogenital organs.

15 Claims, No Drawings

LACTIC ACID BACTERIA-CONTAINING PROBIOTICS PRODUCTS

TECHNICAL FIELD

The present invention relates to lactic acid bacteria isolated from the human digestive tract and a probiotics product containing such lactic acid bacteria as an effective component and prophylactic and/or therapeutic compositions for digestive tract's diseases and urinogenital infectious diseases, which contain the lactic acid bacteria.

BACKGROUND ART

In Japan, there have long been used *Lactobacillus* preparations as drugs for controlling intestinal functions, which have considerably high safety. Moreover, there have also been put on the market a variety of so-called health foods for controlling intestinal functions, which contain lactic acid bacteria. In addition, yogurt and fermented milk comprising lactic acid bacteria, conventionally favorably ingested as health foods have recently been admitted as specific health foods for controlling the gastrointestinal conditions and have thus attracted special interest. On the other hand, lactic acid bacteria-containing drugs and foods have likewise been attracted special interest as representatives of "probiotics products", which show not only the effect of controlling intestinal functions, but also other various functions and are thus effective for maintaining the user's health, even in Europe and America and various kinds of products have commercially been available. For this reason, lactic acid bacteria have widely been investigated for the study and development of various probiotics products (Reuter G.: Intraintestinal Flora and Probiotics (edited by MITSUOKA Tomotari), pp. 17–39, published by Gakkai Shuppan Center, 1998).

The term "probiotics" is in general defined to be "living microorganisms capable of improving the balance of the enterobacterial flora in a host to thus bring beneficial effects on the host" (Fuller R.: Gut, 1991, 32:439–42). In addition, it has been reported that the probiotics typically represented by lactic acid bacteria possess a wide variety of functions as will be detailed below (Sanders M E & Huis in't Veld J: Antonie van Leeuwenhoek, 1999, 76: 293–315): 1) Assistance of lactose-digestion; 2) resistance to enterobacteria; 3) inhibition of the occurrence of colon cancer; 4) inhibition of small intestinal bacteria-excess proliferation; 5) immunomodulating effects; 6) anti-allergic effects; 7) effects of reducing blood lipid concentration; 8) hypotensive effects; 9) inhibition of urinary tract-infection; 10) inhibition of *Helicobacter pylori* infection; and 11) inhibition of hepatic encephalopathy. Moreover, it has also been proved that the tooth-brushing with lactic acid bacteria is quite effective even for the prevention or treatment of periodontitis (IMAI, Tatsuya: Tooth-Brushing with Lactic Acid Bacteria for Curing Periodontitis Within 3 Days, published by MAKINO Publishing Company, 2000).

As has been discussed above, it has been elucidated that the probiotics may improve the balance of not only the enterobacterial flora, but also bacterial florae in oral cavity, stomach and other digestive tracts as well as urinogenital bacterial flora such as the intra-vaginal flora to thus bring beneficial effects on the host. It would be recognized that lactic acid bacteria are adhered to mucous membranes of digestive tracts and urinogenital organs, proliferate thereon, and produce useful metabolites such as lactic acid to directly or indirectly make the barrier function of mucous membranes of digestive tracts and urinogenital organs normal or healthy and to thus show the foregoing effects or functions.

Lactic acid bacteria to be used in probiotics products are selected on the basis of the criteria or requirements such as the stability, the resistance to the acid in the stomach, the resistance to bile, the stability during manufacture of a product or the stability of the bacteria in the product, the adhesion to mucous membranes, the bacterial inhibitory effects and the ability of stimulating immuno responses (Sanders M E & Huis in't Veld J: Antonie van Leeuwenhoek, 1999, 76: 293–315). As strains, which satisfy the foregoing requirements, principally used herein are lactic acid bacteria belonging to the genuses *Lactobacillus, Streptococcus* and *Bifidobacterium*, which are indigenous lactic acid bacteria found in the human digestive tract. In particular, the lactic acid bacteria belonging to the genus *Lactobacillus* have most frequently been used. Among them, preferentially selected and practically used are strains such as *Lactobacillus rhamnosus* GG strain (Japanese Un-Examined Patent Publication (hereunder referred to as "J. P. KOKAI") Sho 61-280433), *Lactobacillus casei* Shirota strain (commercially available under the trade name of "Yakult"), *Lactobacillus johnsonii* La1 strain (J. P. KOKAI Hei 6-315373), *Lactobacillus plantarum* 299 strain (DMS 6595) (TOKUHYO Hei 6-501624), *L. plantarum* 299v strain (DMS 9843) (TOKUHYO Hei 11-502703), *Lactobacillus salivarius* UCC 1 strain (NCIMB 40830) and *L. salivarius* UCC 118 strain (NCIMB 40829) (WO 98/35014).

When these lactic acid bacteria-containing probiotics products are administered to animal and human bodies, however, a problem arises such that the lactic acid bacteria are discharged soon from, for instance, digestive tract and therefore, the products fail to maintain and show the desired functions of probiotics.

DISCLOSURE OF THE INVENTION

In consideration of the foregoing circumstances, it is an object of the present invention to provide lactic acid bacteria, which can highly maintain their probiotics' functions in the digestive tract without being discharged therefrom and have high colonization ability, a probiotics product containing such lactic acid bacteria as an effective component and prophylactic and/or therapeutic compositions for digestive tract's diseases and urinogenital infectious diseases, which contain the lactic acid bacteria.

Accordingly, the present invention provides a probiotics product containing, as an effective component, lactic acid bacteria belonging to *Lactobacillus salivarius*, which are highly adhesive to mucous membranes and have high proliferation ability and high resistance to acids.

The present invention likewise provides prophylactic and/or therapeutic compositions for digestive tract's diseases, which contain, as an effective component, lactic acid bacteria belonging to *Lactobacillus salivarius*, which are highly adhesive to mucous membranes and have high proliferation ability and high resistance to acids.

The present invention also provides prophylactic and/or therapeutic compositions for urinogenital infectious diseases, which contain, as an effective component, lactic acid bacteria belonging to *Lactobacillus salivarius*, which are highly adhesive to mucous membranes and have high proliferation ability and high resistance to acids.

Furthermore, the present invention provides novel *Lactobacillus salivarius* WB21 strain (FERM BP-7792), which is highly adhesive to mucous membranes and has high proliferation ability and high resistance to acids.

The inventors of this invention have succeeded in the selection, from the human-derived lactic acid bacteria, of lactic acid bacteria, which are optimum for use as probiotics products and which are highly adhesive to mucous membranes and have high proliferation ability and high resistance to acids, as compared with the lactic acid bacteria used in the conventional probiotics products and have thus completed the present invention. The present invention will hereunder be described in more detail.

BEST MODE FOR CARRYING OUT THE INVENTION

In the present invention, principally used comparative strains are *Lactobacillus rhamnosus* GG Strain (ATCC 53103) (J. P. KOKAI Sho 61-280433) and *Lactobacillus johnsonii* La1 strain (CNCM I-1225) (J. P. KOKAI Hei 6-315373). These strains are selected on the basis of the adhesiveness to digestive tract's mucous membranes as a selection standard, probiotics products, which make use of these strains, have widely been put on the market in all the countries of the world and there have been known a large number of reports on the usefulness of these products. The inventors of this invention have conducted various investigations for the selection, from lactic acid bacteria living in human intestine, of lactic acid bacteria, which are highly adhesive to mucous membranes and have high proliferation ability and high resistance to acids, as compared with the comparative lactic acid bacteria and as a result, have found out *Lactobacillus salivarius* WB1004 strain (FERM BP-7791) as a strain satisfying the foregoing requirements. The bacteriological characteristics or the like of this strain are disclosed in J. P. KOKAI Hei 9-241173 as lactic acid bacteria possessing an ability of eliminating *Helicobacter pylori* from the stomach and the duodenum.

The inventors of this invention have further repeatedly conducted selection of strains surviving even after the treatment of *Lactobacillus salivarius* WB1004 strain under low pH conditions (this treatment comprising suspending the strain in an HCl/KCl buffering solution having a pH value of 1.2 to 1.4 and containing 0.9% NaCl and then incubating the strain at 37° C. for 30 minutes) for the purpose of selecting the strain having higher resistance to acids. As a result, the inventors of this invention have found out *Lactobacillus salivarius* WB21 strain whose survival rate at a low pH value or in a low pH treatment is 10 to 100 times higher than that observed for *Lactobacillus salivarius* WB1004 strain. The bacteriological characteristics of this strain will be given in the following Table 1.

*Lactobacillus salivarius* WB1004 strain and *Lactobacillus salivarius* WB21 strain were deposited with the Independent Administrative Juridical Person: Industrial Technology Comprehensive Research Laboratories, Deposition Center of Microorganism for Patent Application, 305-8566, Chuo 6$^{th}$, Higashi 1-Chome 1-Banchi 1, Tsukuba-City, Ibaraki-Ken under the accession numbers of FERM BP-7791 (deposition Date: Heisei 7 (1995), Dec. 12) and FERM BP-7792 (deposition Date: Heisei 12 (2000), Apr. 14).

*Lactobacillus salivarius* strain WB21 was deposited on Aug. 14, 2000 under accession number FERM BP-7792 (which was originally deposited on Apr. 14, 2000 under the accession number of FERM P-17991).

*Lactobacillus salivarius* strain WB1004 was deposited on Aug. 14, 2000 under accession number of FERM BP-7791 (which was originally deposited on Apr. 14, 2000 under the accession number of FERM P-15360).

Both *Lactobacillus salivarius* strains were deposited under the terms of the Budapest Treaty at the Independent Administrative Juridical Person: Industrial Technology Comprehensive Research Laboratories, Deposition Center of Microorganism for Patent Application, Chuo 6$^{TH}$, Higashi 1-Chome 1-Banchi 1, Tsukuba-City, Ibaraki-Ken, Japan.

All restrictions on the availability to the public of the material so deposited will be irrevocably removed upon the granting of a patent.

TABLE 1

Bacteriological Characteristics of *Lactobacillus salivarius* WB21 strain

| Morphological Properties: | |
| --- | --- |
| Shape of cell | Bacillus |
| Size of cell | 0.7 to 0.9 × 1.6 to 4.5 μm |
| Mobility | − |
| Presence of Spore | − |
| Gram staining | + |
| Physiological Characteristics: | |
| Gas Production | − |
| Catalase | − |
| Behavior to oxygen | Facultative anaerobe |
| Liquefaction of gelatin | − |
| Reduction of nitrate | − |
| Indole-production | − |
| Hydrogen sulfide-production | − |
| Optical rotatory power of resulting lactic acid | L |
| Ability of growing at 15° C. | − |
| Fermentation of sugars: | |
| Amygdaline | − |
| Arabinose | − |
| Cellobiose | − |
| Esculin | − |
| Fructose | + |
| Galactose | + |
| Glucose | + |
| Gluconic acid | − |
| Lactose | + |
| Maltose | + |
| Mannitol | + |
| Mannose | + |
| Melezitose | − |
| Melibiose | + |
| Raffinose | + |
| Rhamnose | + |
| Ribose | − |
| Salicin | − |
| Sorbitol | + |
| Sucrose | + |
| Trehalose | + |
| Xylose | − |

The adhesion to mucosal epithelial cells, proliferation ability and resistance to acids of *Lactobacillus salivarius* WB1004 strain (FERM BP-7791) and *Lactobacillus salivarius* WB21 strain (FERM BP-7792) are as follows:

Adhesion to Mucosal Epithelial Cells

The mucosal epithelial cells used herein were those used in the usual methods such as carcinoma cells of human large intestine Caco2 (ATCC HTB-37, Coconnier M H et al.: FEMS Microbiol. Lett., 1993, 110: 299), human colon carcinoma cells HT-29 (ATCC HTB-38) and small intestinal epithelial cells derived from human fetus Intestine-407 (ATCC CCL-6) for models of intestinal tract's mucous membrane cells; human gastric carcinoma cells MKN45 (JCRB 0254, YAMAGUCHI Haruyuki et al.: Bulletin of Infectious Disease Society, 1998, 72: 487) for models of stomach mucous membrane cells; and human basis oral cavity-squamous cell carcinoma-derived cells HO-1-u-1 (JCRB 0828, MIYAUCHI Shinobu et al., Bulletin of Stomatological Surgery Society in Japan, 1985, 31: 1347) and human buccal mucous membrane-squamous cell carcinoma-derived cells HO-1-N-1 (JCRB 0831, MOROYAMA Takamasa et al., Descriptions of the General Meeting of Japanese Cancer Association, 1986, 45: 242) for models of oral cavity mucous membrane cells. The adhesion was investigated and evaluated in accordance with the method of Granato et al. (Appl. Environ. Microbiol., 1999, 65: 1071).

Caco2 cells were suspended in a DMEM medium (available from Sigma Company) containing 20% fetal calf serum such that the cell concentration was equal to $1\times10^4$ cells/mL and the resulting cell suspension was dispensed in a 24-well microplate (1 mL per well). The cultivation was conducted at 37° C. for 16 days while exchanging the culture medium every two days. The Caco2 cells adhered to the microplate were washed three times with 1 mL of PBS. After culturing the monolayer cells with MRS broth (available from Difco Company) overnight, there was added 1 mL of a suspension of each lactic acid bacterial strain obtained by dispersing each lactic acid bacterial cells in PBS (phosphate-buffered saline available from Nissui Seiyaku K.K.) to a viable cell count of about $5\times10^8$ cells/mL to the monolayer cells and the mixture was incubated in a 10% $CO_2$ incubator at 37° C. for 30 minutes. Thereafter, the monolayer of the Caco2 cells was washed three times with 1 mL each of PBS to remove the lactic acid bacteria, which were not adhered to the mucosal epithelial cells, followed by subjecting the monolayer to gram staining and the determination of the number of adhered lactic acid bacteria using a light microscope. As a result, it could be confirmed that the adhesiveness of the lactic acid bacterium of the present invention belonging to Lactobacillus salivarius to the Caco2 cells was considerably higher than those observed for Lactobacillus rhamnosus GG strain (ATCC53103), Lactobacillus johnsonii La1 strain (CNCM I-1225), Lactobacillus plantarum 299 strain (DSM6595), L. plantarum 299v strain (DSM9843) and other standard strains of human intra-intestinal lactic acid bacteria. It was proved that Lactobacillus salivarius WB1004 strain and Lactobacillus saivarius WB21 strain showed particularly high adhesiveness, among others (see Table 2).

TABLE 2

Adhesiveness of Lactic Acid Bacteria to Human Colon Cancer Cell Caco2

| Strain | Number of adhered lactic acid bacterial cells per 100 Caco2 cells (average for n = 3) |
|---|---|
| Lactobacillus salivarius WB1004 | 130 |
| Lactobacillus salivarius WB21 | 190 |
| Lactobacillus salivarius CIP103140 | 70 |
| Lactobacillus salivarius JCM1150 | 72 |
| Lactobacillus salivarius UCC1 | 90 |
| Lactobacillus salivarius UCC118 | 190 |
| Lactobacillus rhamnosus GG | 15 |
| Lactobacillus johnsonii La1 | 11 |
| Lactobacillus paracasei CIP103918 | 6 |
| Lactobacillus plantarum JCM1149 | 29 |
| Lactobacillus plantarum 299 | 25 |
| Lactobacillus plantarum 299v | 76 |
| Lactobacillus gasseri JCM1131 | 38 |
| Lactobacillus acidophilus CIP76.13 | 9 |
| Lactobacillus casei CIP103137 | 0 |
| Lactobacillus fermentum JCM1173 | 3 |

The same cultivation procedures used above were repeated except that HT-29 and Intestine-407 cells were substituted for Caco2 cells and that a Fischer's medium (available from GIBCO BRL Company) containing 10% fetal calf serum to examine the adhesiveness of lactic acid bacteria to these HT-29 and Intestine-407 cells. As a result, it could be confirmed that the adhesiveness of the Lactobacillus salivaris WB21 strain according to the present invention to these cells was considerably higher than those observed for Lactobacillis rhamnosus GG strain, Lactobacillus johnsonii La1 strain, Lactobacillus plantarum 299 strain, L. plantarum 299v strain, Lactobacillus salivarius UCC 1 strain and L. salivarius UCC 118 strain (see Table 3).

TABLE 3

Adhesiveness of Lactic Acid Bacteria to Human Colon Cancer Cell HT-29 and Small Intestinal Epithelial Cells Intestine-407 derived from Human Fetus

| Strain | Number of adhered lactic acid bacterial cells per 100 Cancer cells (average for n = 3) | |
|---|---|---|
| | HT-29 | Intestine-407 |
| Lactobacillus salivarius WB21 | 173 | 177 |
| Lactobacillus salivarius UCC 1 | 55 | 26 |
| Lactobacillus salivarius UCC 118 | 49 | 30 |
| Lactobaciiius rhamnosus GG | 25 | 9 |
| Lactobacillus johnsonii La1 | 31 | 13 |
| Lactobacillus plantarum 299 | 9 | 54 |
| Lactobacillus plantarum 299v | 16 | 16 |

MKN45 Cells were suspended in an RPMI1640 medium (available from Nissui Seiyaku K.K.) containing 10% fetal calf serum to a cell concentration of $5\times10^4$ cells/mL and the resulting cell suspension was dispensed in a 96-well microplate (0.1 mL per well). The cultivation of the cell suspension was conducted at 37° C. for 3 days and then the MKN45 cells adhered to the microplate were washed three times with PBS. To the resulting monolayer of the MKN45 cells, there was added 0.1 mL each of a suspension of each lactic acid bacterial strain prepared by dispersing each lactic acid bacteria in PBS (phosphate-buffered saline, available from Nissui Seiyaku K.K.) such that the viable cell count was equal to about $5\times10^8$ cells/mL after cultivating the monolayered MKN45 cell in MRS broth (available from Difco Company) overnight and then the resulting mixture was incubated at 37° C. for 10 minutes. Thereafter, the monolayer of the MKN45 cells was washed three times with PBS to thus remove the un-adhered lactic acid bacteria, followed by subjecting the monolayer to gram staining and the determination of the number of adhered lactic acid bacterial cells using a light microscope. As a result, it could be confirmed that the adhesiveness of the lactic acid bacterium of the present invention belonging to Lactobacillus salivarius to the MKN45 cells was considerably higher than those observed for Lactobacillus rhamnosus GG strain, Lactobacillus johnsonii La1 strain and other standard strains of human intra-intestinal lactic acid bacteria. It was proved that Lactobacillus salivarius WB1004 strain and Lactobacillus salivarius WB21 strain showed particularly high adhesiveness, among others (see Table 4).

TABLE 4

Adhesiveness of Lactic Acid Bacteria to Human Gastric Carcinoma Cell MKN45

| Strain | Number of adhered lactic acid bacterial cells per 100 MKN45 cells (average for n = 4) |
|---|---|
| Lactobacillus salivarius WB1004 | 172 |
| Lactobacillus salivarius WB21 | 180 |
| Lactobacillus salivarius CIP103140 | 82 |
| Lactobacillus salivarius JCM1150 | 78 |
| Lactobacillus rhamnosus GG | 8 |
| Lactobacillus johnsonii La1 | 13 |
| Lactobacillus paracasei CIP103918 | 0 |
| Lactobacillus plantarum JCM1149 | 0 |
| Lactobacillus gasseri JCM1131 | 37 |
| Lactobacillus acidophilus CIP76.13 | 0 |
| Lactobacillus casei CIP103137 | 0 |
| Lactobacillus fermentum JCM1173 | 12 |

HO-1-u-1 (JCRB0828) Cells were suspended in a DMEM/F12 (1:1) medium (available from GIBCO BRL Company) containing 10% fetal calf serum to a cell concentration of $2\times10^4$ cells/mL and the resulting cell suspension was dispensed in a 96-well microplate (0.1 mL per well). After cultivating the suspension at 37° C. for 4 days, the HO-1-u-1 cells adhered to the microplate were washed three times with PBS. To the resulting monolayered HO-1-u-1 cells thus formed, there was added 0.1 mL each of a suspension of each lactic acid bacterial strain prepared by dispersing each lactic acid bacteria in PBS (phosphate-buffered saline available from Nissui Seiyaku K.K.) such that the viable cell count was equal to about $1\times10^9$ cells/mL after cultivating the monolayered HO-1-u-1 cells in MRS broth (available from Difco Company) overnight and then the resulting mixture was incubated at 37° C. for 10 minutes. Thereafter, the monolayer of the HO-1-u-1 cells was washed three times with PBS to thus remove the un-adhered lactic acid bacteria, followed by subjecting the monolayer to gram staining and the determination of the number of adhered lactic acid bacterial cells using a light microscope. As a result, it could be confirmed that the adhesiveness of the Lactobacillus salivarius WB1004 strain and Lactobacillus salivarius WB21 strain to the HO-1-u-1 cells were considerably higher than those observed for Lactobacillus rhamnosus GG strain and Lactobacillus johnsonii La1 strain (see Table 5).

TABLE 5

Adhesiveness of Lactic Acid Bacteria to Human Basis Oral Cavity-Squamous Cell Carcinoma-derived Cells HO-1-u-1

| Strain | Number of adhered lactic acid bacterial cells per 100 Cancer cells (average for n = 3) |
|---|---|
| Lactobacillus salivarius WB1004 | 307 |
| Lactobacillus salivarius WB21 | 294 |
| Lactobacillus rhamnosus GG | 26 |
| Lactobacillus johnsonii La1 | 21 |

HO-1-N-1 (JCRB0831) cells were suspended in a DMEM/F12 (1:1) medium (available from GIBCO BRL Company) containing 10% fetal calf serum to a cell concentration of $2\times10^4$ cells/mL and the resulting cell suspension was dispensed in a 96-well microplate (0.1 mL per well). After cultivating the suspension at 37° C. for 4 days, the HO-1-N-1 cells adhered to the microplate were washed three times with PBS. To the resulting monolayered HO-1-N-1 cells thus formed, there was added 0.1 mL each of a suspension of each lactic acid bacterial strain prepared by dispersing each lactic acid bacteria in PBS (phosphate-buffered saline available from Nissui Seiyaku K.K.) such that the viable cell count was equal to about $1\times10^9$ cells/mL after cultivating the monolayered HO-1-N-1 cells in MRS broth (available from Difco Company) overnight and then the resulting mixture was incubated at 37° C. for 10 minutes. Thereafter, the monolayer of the HO-1-N-1 cells was washed three times with PBS to thus remove the un-adhered lactic acid bacteria, followed by subjecting the monolayer to gram staining and the determination of the number of adhered lactic acid bacterial cells using a light microscope. As a result, it could be confirmed that the adhesiveness of the Lactobacillus salivarius WB1004 strain and Lactobacillus salivarius WB21 strain to the HO-1-N-1 cells were considerably higher than those observed for Lactobacillus rhamnosus GG strain and Lactobacillus johnsonii La1 strain (see Table 6).

TABLE 6

Adhesiveness of Lactic Acid Bacteria to Human Buccal Mucous Membrane- Squamous Cell Carcinoma-Derived Cells HO-1-N-1

| Strain | Number of adhered lactic acid bacterial cells per 100 cancer cells (average for n = 3) |
|---|---|
| Lactobacillus salivarius WB1004 | 164 |
| Lactobacillus salivarius WB21 | 205 |
| Lactobacillus rhamnosus GG | 60 |
| Lactobacillus johnsonii La1 | 22 |

Proliferation Ability

Each lactic acid bacterial strain pre-cultured with MRS broth (at 37° C. for 18 hours) was inoculated into MRS broth and subjected to standing culture at 37° C. After 9 hours, the culture broth was appropriately diluted with PBS, smeared onto MRS agar (available from Difco Company) and cultured at 37° C. for 24 hours according to anaerobic culture. The number of colonies formed was counted to determine the colony forming units (cfu) and to thus evaluate the proliferation ability. As a result, the proliferation abilities of the lactic acid bacteria according to the present invention were found to be considerably higher than those observed for Lactobacillus rhamnosus GG strain and Lactobacillus johnsonii La1 strain as well as other lactic acid bacteria (see Table 7).

TABLE 7

Proliferation Ability of Lactic Acid Bacteria

| Strain | Viable Cell Number (cfu/mL) |
|---|---|
| Lactobacillus salivarius WB1004 | $2.9 \times 10^9$ |
| Lactobacillus salivarius WB21 | $3.4 \times 10^9$ |
| Lactobacillus rhamnosus GG | $2.1 \times 10^7$ |
| Lactobacillus johnsonii La1 | $2.6 \times 10^8$ |
| Lactobacillus casei Shirota | $1.9 \times 10^7$ |
| Lactobacillus gasseri JCM1131 | $1.5 \times 10^7$ |

Resistance to Acids

To an artifical gastric juice (MRS broth to which sugar-containing pepsin was added to a concentration of 0.32% and whose pH value was adjusted to 3 with HCl), there was added each lactic acid bacterial strain to a cell concentration of about $1 \times 10^8$ cells/mL and the resulting mixture was allowed to stand at 37° C. After 3 hours, the artificial gastric juice was appropriately diluted with PBS, smeared onto BL Agar (available from Nissui Seiyaku K.K.) and cultured at 37° C. for 24 hours according to anaerobic culture. The number of colonies formed was counted to determine the number of the colony forming units and to thus evaluate the resistance to acids. As a result, the resistance to acid of the lactic acid bacteria according to the present invention was found to be considerably higher than those observed for *Lactobacillus rhamnosus* GG strain and *Lactobacillus johnsonii* La1 strain (see Table 8).

TABLE 8

Resistance to Acid of Lactic Acid Bacteria in Artificial Gastric Juice

| Strain | Survival Rate (%) |
|---|---|
| *Lactobacillus salivarius* WB1004 | 100 |
| *Lactobacillus salivarius* WB21 | 100 |
| *Lactobacillus rhamnosus* GG | 54 |
| *Lactobacillus johnsonii* La1 | 82 |

Diseases to which the probiotics products (drugs or foods) of the present invention can be applied for the prevention, sanitation or treatment thereof may be any one insomuch as the pharmacological action based on the functions of the conventional probiotics products can be ensured for such diseases, but there may particularly be listed, for instance, various diseases of digestive tracts including oral cavity and ulinogenital infectious diseases. The term "diseases of digestive tract" used herein means, for instance, food intoxication; diseases of oral cavity such as dental caries and periodontitis; gastrointestinal diseases such as diarrhea, constipation, loose stool (or passage) and abdominal inflation; inveterate inflammatory enteropathies represented by infectious diseases of digestive tract, hypersensitive intestinal syndromes, ulcerous colitis and Crohn's disease; and a variety of symptoms and diseases such as food allergy, pseudomembranous colitis, hemorrhagic colitis, gastritis, gastroduodenal ulcer.

When the probiotics product of the present invention is a drug, the dosage forms thereof may preferably be, for instance, powders, granules, tablets, capsules and syrups and these drugs may be administered through the oral route. These various kinds of pharmaceutical preparations may be prepared by incorporating, into the basis, known auxiliary agents currently used in the field of drug-manufacturing techniques such as excipients, binders, disintegrators, coating agents, lubricants, stabilizers, corrigents, solubilizing agents, suspending agents and diluents, according to the usual method. The dose for human bodies may vary depending on, for instance, the kind of disease to be treated, the purpose of use (prevention, sanitation or treatment) and the age of a patient, but the dose for adult is not less than $1 \times 10^6$ cells/day and preferably $1 \times 10^8$ to $1 \times 10^{12}$ cells/day as expressed in terms of the number of surviving bacterial cells, which may be administered at a time or in several portions. However, the lactic acid bacteria of the present invention may be administered in a large amount beyond the foregoing range without any problem since the lactic acid bacteria are highly safe.

When the probiotics products of the present invention are foods, they can be ingested in the form of fermented milk typically represented by yogurt, lactic acid bacteria-containing beverages, powdered foods, granular foods, paste-like foods and tablet-like foods. These foods can be prepared from the ingredients used for the preparation thereof according to the usual method. For instance, starter bacteria such as *Lactobacillus bulgaricus*, *Lactobacillus acidophilus*, *Lactobacillus herbeticus*, *Streptococcus thermophilus* and *Streptococcus lactis* or dairy lactic acid bacteria are inoculated into milk of cow or sheep, together with the lactic acid bacteria of the present invention and then subjected to mixed cultivation or mixed after the independent cultivation to thus give fermented milk. The lactic acid bacteria of the present invention are subjected to axenic culture, followed by the recovery of bacterial cells by, for instance, centrifugation, lyophilization thereof using an appropriate stabilizer to give lyophilized bacterial bodies and manufacture of a powdery food, a granular food or a tablet-like food using the lyophilized bacterial bodies, according to the usual method.

The amount of the effective component may arbitrarily be selected and may appropriately be determined depending on the purpose of use (prevention, sanitation or treatment) and may be not less than $1 \times 10^6$ cells/day and preferably $1 \times 10^8$ to $1 \times 10^{12}$ cells/day as expressed in terms of the number of surviving bacterial cells, which may be administered at a time or in several portions. When ingesting the effective component over a long period of time for sanitation and for maintaining the health, however, the amount thereof may be smaller than the foregoing range or the lactic acid bacteria of the present invention may be ingested in a large amount beyond the foregoing range without any problem since the lactic acid bacteria are highly safe.

EXAMPLE

The present invention will be described in more detail below with reference to the following Test Examples and Examples, but the present invention is not restricted to these specific Examples at all. In the following description, the term "%" means "% by mass" unless otherwise specified.

Test Example 1

Test of Lactic Acid-production by Lactic Acid Bacteria Adhered to Mucous Epithelial Cells To confirm that the *Lactobacillus salivarius* bacteria according to the present invention adhered to mucous epithelial cells proliferate and produce lactic acid as a useful metabolite, the amount of lactic acid produced by the lactic acid bacteria adhered to the cells was examined. More specifically, Caco2 cells were suspended in a DMEM medium containing 20% fetal calf serum to a cell concentration of $1 \times 10^4$ cells/mL and then the resulting suspension was dispensed into a 24-well microplate (1 mL per well). The cultivation was conducted at 37° C. for 16 days while exchanging the culture medium every two days. The Caco2 cells adhered to the microplate were washed three times with 1 mL of PBS. After culturing the monolayer cells with MRS broth overnight, there was added 1 mL of a suspension of each lactic acid bacterial strain obtained by dispersing each lactic acid bacterial cells in PBS (phosphate-buffered saline available from Nissui Seiyaku K.K.) to a viable count of about $5 \times 10^8$ cells/mL to the monolayer cells and the mixture was incubated in a 10% $CO_2$ incubator at 37° C. for 30 minutes. Thereafter, the monolayer of the Caco2 cells was washed three times with 1 mL each of PBS to remove the un-adhered lactic acid bacteria, 1 mL of MRS broth was added and the lactic acid bacteria adhered were cultured at 37° C. After 6 hours, the amount of lactic acid thus produced was quantitatively analyzed by the gas chromatography technique. As a result, the amount of the lactic acid produced by the lactic acid bacteria of the present invention adhered to the mucous epithelial cells was found to be considerably higher than those observed for *Lactobacillis rhamnosus* GG strain and *Lactobacillus johnsonii* La1 strain (see Table 9).

TABLE 9

Test for lactic acid production by lactic acid bacteria adhered to mucous epithelial cells

| Strain | Amount of Lactic Acid Produced (mM) |
|---|---|
| Lactobacillus salivarius WB21 | 59 |
| Lactobacillus rhamnosus GG | 4 |
| Lactobacillus johnsonii La1 | 6 |

Test Example 2

Test for the Inspection of Lactic Acid Bacteria for the Effect of Inhibiting Bacteria in Food Poisoning In this Test Example, the *Lactobacillus salivarius* of the present invention was inspected for the effect of controlling or inhibiting pathogenic bacteria in food poisoning. *Staphylococcus aureus* ATCC25923, *Salmonella enteritidis* 116-54, enterotoxigenic *Escherichia coli* WHO 43 and *Vibrio parahaemolyticus* (ATCC17802) were used as such pathogenic bacteria in food poisoning. A GAM liquid medium (available from Nissui Seiyaku K.K.) to which glucose had been added to a concentration of 1% was used as a test culture medium. Lactic acid bacteria were inoculated into the test culture medium, *Vibrio parahaemolyticus* cells were inoculated into a GAM liquid medium and other pathogenic bacteria in food poisoning were inoculated into a BHI liquid culture medium (available from Difco Company), followed by the pre-cultivation at 37° C. overnight. Each pathogenic bacterium in food poisoning and the pre-culture of each lactic acid bacterium (1% each) were inoculated into 100 mL of the test culture medium. Each culture medium was subjected to standing culture at 37° C. and the number of surviving cells of each pathogenic bacterium in food poisoning was counted with the elapse of time. There were used a DHL agar medium (available from Nissui Seiyaku K.K.) for the measurement of *Salmonella* and enterotoxigenic *Escherichia coli*; a *Staphylococcus* 110 agar medium (available from Nissui Seiyaku K.K.) for *Staphylococcus aureus*; and a TCBS agar medium for *Vibrio parahaemolyticus* (available from Nissui Seiyaku K.K.). As a result, it was proved that *Lactobacillus salivarius* WB21 had strong action of controlling or inhibiting pathogenic bacteria in food poisoning (see Table 10).

TABLE 10

Test for inspecting lactic acid bacteria for the effect of controlling pathogenic bacteria in food poisoning

| | Number of Viable Count ($Log_{10}CFU/mL$) | | | |
|---|---|---|---|---|
| Strain | S. aureus (12)* | Salmonella enteritidis (24) | Entero-toxigenic Escherichia coil (24) | Vibrio parahae-molyticus (12) |
| Control | 5.32 | 9.10 | 9.10 | 7.13 |
| Lactobacillus salivarius WB21 | 1.60 | <1 | 6.81 | <1 |
| Lactobacillus johnsonii La1 | 2.48 | <1 | 8.78 | <1 |
| Lactobacillus rhamnosus GG | 3.00 | 6.04 | 8.85 | <1 |
| Lactobacillus salivarius UCC118 | 5.20 | 4.76 | 8.08 | <1 |

*: The numerical value given in the parentheses means the cultivation time.

Test Example 3

Test for Examining the Adhesion of Lactic Acid Bacteria to Digestive Tract of Mouse In this Test Example, tests were conducted using mice for examining the adhesiveness of *Lactobacillus salivarius* of the present invention, in vivo, to the digestive tract. Drinking water to which 200 μg/mL of amoxicillin and 10 μg/mL of vancomycin had been added was fed to ICR mice (male, 5-week-old) for 5 days to thus eliminate the bacteria in the digestive tract or sterilize the tract. To mice which were fasted for 18 hours, there was administered, through oral route, 0.1 mL each of a liquid obtained by cultivating lactic acid bacteria in MRS broth at 37° C. for 18 hours, collecting the cultivated lactic acid bacteria and suspending the bacterial cells in PBS to a cell concentration of about $10^9$/mL. These animals were slaughtered after one hour from the administration, the abdominal region thereof was incised and the small intestine thereof was washed three times by administering PBS to the small intestine through the stomach using a sonde. After the washing, the small intestine was removed and incised. Moreover, another group of animals were slaughtered after six hours from the administration, the colons of these animals were removed, incised and then washed three times with PBS. To each organ, there was added PBS in an amount of 9 times the weight of the organ, followed by the homogenization of the organ with a homogenizer, the appropriate dilution with PBS and the subsequent smearing thereof onto an LBS agar culture medium (available from BBL Company). After the cultivation at 37° C. for 2 days according to the anaerobic culture, the number of colonies formed were counted to thus determine the number of lactic acid bacterial cells adhered to each organ. As a result, it was proved that the adhesiveness of *Lactobacillus salivarius* WB21 strain according to the present invention to the mucous membrane of the digestive tract was higher than those observed for *Lactobacillus rhamnosus* GG strain and *Lactobacillus johnsonii* La1 strain (see Table 11).

TABLE 11

Test for the examination of the adhesiveness of lactic acid bacteria to the digestive tract

| Strain | Number of bacterial cells adhered to small intestine ($Log_{10}CFU/g$) | Number of bacterial cells adhered to colon ($Log_{10}CFU/g$) |
|---|---|---|
| Lactobacillus salivarius WB21 | 6.6 ± 0.4 | 5.7 ± 0.3 |
| Lactobacillus rhamnosus GG | 5.9 ± 0.6 | 5.6 ± 0.1 |
| Lactobacillus johnsonii La1 | 5.2 ± 1.1 | 4.9 ± 0.5 |

The number of adhered bacterial cells means the average (n=3)±standard deviation.

Test Example 4

Test for the Inspection of Lactic Acid Bacteria for the Control of Pathogenic Bacteria in the Oral Cavity In this Test Example, *Lactobacillus salivarius* of the present invention was inspected for the ability of controlling pathogenic bacteria present in the oral cavity. As pathogenic bacteria in oral cavity, the dental caries-causing bacterium (*Streptococcus mutans* JCM5705) and the periodontal disease-causing bacterium (*Porphyromonas gingivalis* JCM8525) were used herein. A GAM liquid medium (available from Nissui Seiyaku K.K.) to which glucose had been added to a concentration of 1% was used as a test culture medium. Each strain was inoculated into the test culture medium and then pre-cultured at 37° C. overnight. The pathogenic bacteria and the pre-culture of the lactic acid bacteria (1% each) were inoculated into 100 mL of the test culture medium to thus conduct independent cultivation and mixed cultivation with the lactic acid bacteria and the culture broth was sampled with the elapse of time. Each sample of the culture broth was appropriately diluted and the number of survival pathogenic bacterial cells in the oral cavity was determined using the following culture medium and under the following culture conditions.

The dental caries-causing bacterium: Cultivated in a GAM agar culture medium (available from Nissui Seiyaku K.K.) to which bacitracin was added to a final concentration of 10 μg/mL at 37° C. for 3 days according to the anaerobic culture.

The periodontal disease-causing bacterium: Cultured in an EG agar culture medium to which gentamicin sulfate was added to a final concentration of 10 μg/mL (MITSUOKA Tomotari edition, Enterobacteriology, p. 475, published by Asakura Publishing Company in 1990), at 37° C. for 3 days according to the anaerobic culture.

As a result, it was confirmed that *Lactobacillus salivarius* WB21 strain showed strong ability of controlling the pathogenic bacteria in the oral cavity (see Table 12).

TABLE 12

Test for the inspection of lactic acid bacteria for the control of pathogenic bacteria in the oral cavity

| Strain | Number of surviving bacterial cells ($Log_{10}$CFU/mL) | |
|---|---|---|
| | Dental caries-causing bacterium (16)* | Periodontal disease-causing bacterium (9) |
| Control | 9.16 | 8.33 |
| *Lactobacillus salivarius* WB21 | 5.80 | <1 |

*: The numerical value given in the parentheses means the cultivation time.

Test Example 5

Effect of *Lactobacillus salivarius* WB21 on Insoluble Glucan-production by Dental Caries-causing Bacteria In this Test Example, *Lactobacillus salivarius* WB21 strain was inspected for the effect of controlling the insoluble glucan-producing ability of dental caries-causing bacteria. As such a dental caries-causing bacterium, *Streptococcus mutans* (JCM5705) was used. A GAM liquid medium (available from Nissui Seiyaku K.K.) to which sucrose had been added to a final concentration of 2% was used as a test culture medium. *Streptococcus mutans* (JCM5705) or *Lactobacillus salivarius* WB21 was pre-cultured at 37° C. overnight using this test culture medium to thus obtain each corresponding bacteria-containing liquid. The dental caries-causing bacteria and/or the lactic acid bacteria (0.1 mL each) were inoculated into 10 mL of the test medium to thus conduct independent culture and mixed cultivation of these bacteria at 37° C. for 24 hours. The resulting culture broth was centrifuged (at 3000 rpm for 20 minutes) to thus recover the precipitates formed (bacterial cells+insoluble glucan) and the precipitates were washed three times with 10 mL each of PBS. The insoluble glucan was dissolved by the addition of 5 mL of 0.1N NaOH solution, followed by centrifugation (at 3000 rpm for 20 minutes) and the recovery of the supernatant. The concentration of saccharides present in the supernatant was determined by the phenol-sulfuric acid method to thus examine the amount of produced insoluble glucan. More specifically, 0.2 mL of a 5% phenol solution and 1 mL of concentrated sulfuric acid were added to 0.2 mL of the supernatant, followed by allowing the resulting mixture to stand for 10 minutes, stirring the mixture and further allowing the mixture to stand for additional 20 minutes. The absorbance of the reaction system at 492 nm was measured to thus calculate the insoluble glucan concentration on the basis of the calibration curve prepared using glucose solutions. As will be seen from the data listed in the following Table 13, *Lactobacillus salivarius* WB21 showed strong effect of controlling the insoluble glucan-producing ability of the dental caries-causing bacteria.

TABLE 13

Effect of *Lactobacillus salivarius* WB21 on insoluble glucan-producing ability of dental caries-causing bacteria
Amount of Insoluble Glucan Produced (μg/mL)

| Dental caries-causing bacteria alone | Dental caries-causing bacteria + *Lactobacillus salivarius* WB21 | *Lactobacillus salivarius* WB21 alone |
|---|---|---|
| 315 | 159 | 45 |

Example 1

Preparation of Dry Bacterial Powder of *Lactobacillus salivarius*

Each strain of *Lactobacillus salivarius* WB1004 and *Lactobacillus salivarius* WB21 was inoculated into a Brick's liver liquid medium (MITSUOKA Tomotari, The World of Enterobacteria, published by Sobun-Sha Publishing Company, 1980) containing 0.3% calcium carbonate and then cultured at 37° C. for 18 to 24 hours according to the standing culture. After the completion of the cultivation, each culture broth was centrifuged at 7000 rpm for 15 minutes to thus obtain concentrated bacterial cells in an amount of 1/100 time that of the culture broth. Then, to each concentrated bacterial bodies, there was added the same volume of a dispersion medium containing 5% by mass of sodium glutamate, 5% by mass of soluble starch, 5% by mass of sucrose and 1% by mass of magnesium sulfate heptahydrate, the pH value of the resulting mixture was adjusted to 7.0, the mixture was frozen at a temperature of not higher than −40° C. and then lyophilized. Each bulk of resulting lyophilized bacterial cells was powdered by passing the same through a sieve of 60 mesh to thus give dry bacterial powders of these two kinds of strains.

Example 2

Preparation of *Lactobacillus salivarius* WB21-Containing Tablets

In accordance with the General Rules for Preparations: "Tablets" in the Pharmacopoeia of Japan, 13$^{th}$ edition, there were uniformly admixed, 2 mg (corresponding to a viable cell count of 5×10$^8$) of the dry bacterial cell powder of *Lactobacillus salivarius* WB21 prepared in Example 1, 61 mg of lactose (having a grade specified in the Pharmacopoeia of Japan), 216.2 mg of starch (having a grade specified in the Pharmacopoeia of Japan), 20 mg of povidone (having a grade specified in the Pharmacopoeia of Japan) as a binder and 0.8 mg of magnesium stearate (having a grade specified in the Pharmacopoeia of Japan) as a lubricant, the resulting mixture was compression-molded into un-coated tablets (300 mg each) in a compression machine, the resulting tablets were further subjected to a film-coating operation using hydroxypropyl cellulose to thus give white film-coated tablets.

The tablet may be used as a medical product for controlling the intestinal functions, in particular, a drug for controlling the intestinal functions (adjustment of the bowel movement), for instance, a drug showing such effects as the relief of constipation and loose passage as well as the elimination of the abdominal inflation.

Example 3

Preparation of *Lactobacillus salivarius* WB21 Cell-Containing Powder

In accordance with the General Rules for Preparations: "Powder" in the Pharmacopoeia of Japan, 13$^{th}$ edition, 1 g of the dry bacterial cell powder of *Lactobacillus salivarius* WB21 prepared in Example 1 was uniformly admixed with 400 g of lactose (having a grade specified in the Pharmacopoeia of Japan) and 600 g of starch (having a grade specified in the Pharmacopoeia of Japan) to thus prepare a powder.

The powder may be used as a medical product for controlling the intestinal functions, in particular, a drug for controlling the intestinal functions (adjustment of the bowel movement), for instance, a drug showing such effects as the relief of constipation and loose passage as well as the elimination of the abdominal inflation.

Example 4

Preparation of Fermented Milk through Mixed Cultivation of Starter Bacteria *Lactobacillus acidophilus* and *Lactobacillus salivarius* WB21

*Lactobacillus acidophilus* cells as starter bacteria for preparing fermented milk were inoculated into a reducing skimmed milk culture medium containing 11.5% skimmed milk, 0.5% yeast extract and 0.03% ascorbic acid and then the cultivation was conducted at 37° C. for 16 hours and the resulting culture was used as a bulk starter. On the other hand, the culture medium containing *Lactobacillus salivarius* WB21 prepared in Example 1 and the bulk starter (the culture medium containing *Lactobacillus acidophilus*) prepared above (5% each) were inoculated into a raw mixture comprising raw milk and skimmed milk and then the cultivation of these bacteria was conducted at 38° C. for 16 hours to thus give fermented milk. As a result, it was confirmed that the fermented milk thus prepared using the lactic acid bacteria of the present invention had good taste and palatability and was delicious and highly fancy product.

Example 5

Preparation of *Lactobacillus salivarius* WB21 Cell-Containing Powdery Health Food To a mixture comprising 40 g of vitamin C or 40 g of an equivalent mixture of vitamin C and citric acid, 100 g of granular sugar and 60 g of an equivalent mixture of corn starch and lactose, there were added and uniformly admixed with 1 g of the dry bacterial cell powder of *Lactobacillus salivarius* WB21 prepared in Example 1, 400 g of lactose (having a grade specified in the Pharmacopoeia of Japan) and 600 g of starch (having a grade specified in the Pharmacopoeia of Japan) to thus prepare a powdery health food.

This powdery health food is a lactic acid bacteria-containing health food, anybody extending from infants to the aged may ingest the same, but one can ingest an appropriate amount thereof for the purpose of the sanitation through the control of the abdominal functions. The health food can likewise be ingested for the prevention or treatment of, for instance, food intoxication, dental caries and periodontitis on the basis of the antibacterial activity as one of probiotics functions of the lactic acid bacteria.

INDUSTRIAL APPLICABILITY

According to the present invention, there can be provided lactic acid bacteria, which can sufficiently show probiotics functions without being easily discharged from, for instance, digestive tract and which have high colonization ability as well as a probiotics product containing the lactic acid bacteria as an effective component.

What is claimed is:

1. A biologically pure culture of *Lactobacillus salivarius* strain WB21 (FERM BP-7792).

2. The biologically pure culture of claim 1 in lyophilized form.

3. A composition comprising the biologically pure culture of claim 1 and at least one pharmaceutically acceptable excipient.

4. The composition of claim 3 in the form of a powder.

5. The composition of claim 3 in the form of a granule.

6. The composition of claim 3 in the form of a tablet.

7. The composition of claim 3 in the form of a capsule.

8. The composition of claim 3 in the form of a syrup.

9. The composition of claim 3, wherein said at least one pharmaceutically acceptable excipient comprises at least one member selected from the group consisting of a binder, disintegrator, coating agent, lubricant, stabilizer, corrigent, solubilizing agent, suspending agent, and diluent.

10. A composition comprising the biologically pure culture of claim 1 and at least one food ingredient.

11. The composition of claim 10 in the form of a powder.

12. The composition of claim 10 in the form of a granule.

13. The composition of claim 10 in the form of a tablet.

14. The composition of claim 10, wherein said at least one food ingredient is a fermented milk product.

15. The composition of claim 10, wherein said at least one food ingredient is selected from the group consisting of a sugar, starch, lactose, citric acid and Vitamin C.

* * * * *